(12) United States Patent
Oh et al.

(10) Patent No.: US 11,707,748 B2
(45) Date of Patent: *Jul. 25, 2023

(54) ELECTRODES FORMED FROM 2D MATERIALS FOR DIELECTROPHORESIS AND SYSTEMS AND METHODS FOR UTILIZING THE SAME

(71) Applicant: Regents of the University of Minnesota, Minneapolis, MN (US)

(72) Inventors: Sang-Hyun Oh, Plymouth, MN (US); Steven John Koester, Edina, MN (US)

(73) Assignee: Regents of the University of Minnesota

(*) Notice: Subject to any disclaimer, the term of this patent is extended or adjusted under 35 U.S.C. 154(b) by 159 days.

This patent is subject to a terminal disclaimer.

(21) Appl. No.: 17/121,285

(22) Filed: Dec. 14, 2020

(65) Prior Publication Data

US 2021/0220840 A1 Jul. 22, 2021

Related U.S. Application Data

(63) Continuation of application No. 16/010,980, filed on Jun. 18, 2018, now Pat. No. 10,888,875.

(Continued)

(51) Int. Cl.
*B03C 5/00* (2006.01)
*G01N 27/447* (2006.01)
(Continued)

(52) U.S. Cl.
CPC .............. *B03C 5/005* (2013.01); *B03C 5/026* (2013.01); *G01N 27/44721* (2013.01);
(Continued)

(58) Field of Classification Search
CPC .......... B03C 5/00–028; B03C 2201/26; G01N 27/44721; G01N 27/44756; G01N 27/48721; G01N 33/48728
See application file for complete search history.

(56) References Cited

U.S. PATENT DOCUMENTS 4,647,362 A * 3/1987 Watanabe .......... G01N 27/3335
   204/411
5,569,367 A * 10/1996 Betts ................ G01N 27/44773
   204/600

(Continued)

FOREIGN PATENT DOCUMENTS

CN   103531482   1/2014
KR   20180033711   4/2018

(Continued)

OTHER PUBLICATIONS

Xie et al., "Development of a 3D Graphene Electrode Dielectrophoretic Device," Journal of Visualized Experiments, Jun. 2014 | 88 | e51696 | 11 pages (Year: 2014).*

(Continued)

*Primary Examiner* — Alexander S Noguerola
(74) *Attorney, Agent, or Firm* — Fish & Richardson P.C.

(57) ABSTRACT

Devices, systems, and methods for applying a dielectrophoretic force on a particle include: a cell defining at least one channel for confining the particle; and a first electrode and a second electrode electrically isolated from the first electrode, at least one of the first and second electrodes being formed from a two-dimensional (2D) material providing an atomically sharp edge. The first and second electrodes are arranged sufficiently close to one another and sufficiently close to the channel such that application of a sufficient voltage across the first and second electrodes generates an electric field in at least part of the channel, the electric field having an electric field gradient sufficient to apply the dielectrophoretic force on the particle in the channel.

20 Claims, 9 Drawing Sheets

Related U.S. Application Data

(60) Provisional application No. 62/521,096, filed on Jun. 16, 2017.

(51) Int. Cl.
*G01N 33/487* (2006.01)
*B03C 5/02* (2006.01)

(52) U.S. Cl.
CPC . *G01N 27/44756* (2013.01); *G01N 33/48721* (2013.01); *G01N 33/48728* (2013.01); *B03C 2201/26* (2013.01)

(56) References Cited

U.S. PATENT DOCUMENTS

| | | | |
|---|---|---|---|
| 7,635,420 | B1 | 12/2009 | Li et al. |
| 10,888,875 | B2 | 1/2021 | Oh et al. |
| 2003/0157587 | A1 | 8/2003 | Gomez et al. |
| 2006/0063183 | A1 | 3/2006 | Segawa et al. |
| 2006/0201811 | A1 | 9/2006 | Hamers et al. |
| 2007/0246364 | A1 | 10/2007 | Amlani et al. |
| 2011/0108422 | A1 | 5/2011 | Heller et al. |
| 2012/0037919 | A1 | 2/2012 | Xu et al. |
| 2013/0248368 | A1 | 9/2013 | Kim et al. |
| 2014/0216935 | A1 | 8/2014 | Vezenov |
| 2014/0291606 | A1 | 10/2014 | Avouris et al. |
| 2017/0028408 | A1 | 2/2017 | Menachery et al. |
| 2017/0292934 | A1 | 10/2017 | Azpiroz et al. |
| 2017/0368557 | A1 | 12/2017 | Chi et al. |
| 2018/0361400 | A1 | 12/2018 | Oh et al. |

FOREIGN PATENT DOCUMENTS

| | | |
|---|---|---|
| KR | 101900049 | 9/2018 |
| KR | 20200074785 | 6/2020 |
| KR | 102134394 | 7/2020 |

OTHER PUBLICATIONS

Pumera et al., "Graphene in biosensing," Mater. Today, Jul. 6, 2011, 14(7-8):308-315.
Suvarnaphaet et al., "Graphene-Based Materials for Biosensors: A Review," Sensors, Sep. 21, 2017, 17(10):2161, 24 pages.
Ameri et al., "Utilization of graphene electrode in transparent microwell arrays for high throughput cell trapping and lysis," Biosensors Bioelectronics., 61:625-630, 2014.
Barik et al., "Dielectrophoresis-Enhanced Plasmonic Sensing with Gold Nanohole Arrays," Nano Lett., 14:2006-2012, 2014.
Barik et al., "Graphene-edge dielectrophoretic tweezers for trapping of biomolecules," Nat. Communications, 8:1867, Nov. 2017, 9 pages.
Barik et al., "Ultralow-Power Electronic Trapping of Nanoparticles with Sub-10 nm Gold Nanogap Electrodes," Nano Lett., 16:6317-6324, 2016.
Bonaccorso et al., "Graphene photonics and optoelectronics," Nature Photonics., 4:611-622, Sep. 2010.
Chen et al., "Label-Free Detection of DNA Hybridization using Transistors Based on CVD Grown Graphene," Biosensors Bioelectronics, 41:103-109, Mar. 2013.
Chou et al., "Electrodeless Dielectrophoresis of Single- and Double-Stranded DNA," Biophys. Journal, 83(4):2170-2179, Oct. 2002.
Cinti et al., "Electrochemical Biosensors for Rapid Detection of Foodborne *Salmonella*: A Critical Overview," Sensors, 17(8):1910, Aug. 2017, 22 pages.
Deen et al., "Graphene-Based Quantum Capacitance Wireless Vapor Sensors," IEEE Sensors Journal, 14(5):1459-1466, Dec. 2013.
Dong et al., "Electrical Detection of DNA Hybridization with Single-Base Specificity Using Transistors Based on CVD-Grown Graphene Sheets," Adv. Mater., 22(14):1649-1653, Apr. 2010.
Ebrish et al., "Operation of multi-finger graphene quantum capacitance varactors using planarized local bottom gate electrodes," Appl. Phys. Letters, 100:143102, Apr. 2012, 4 pages.
Electroschematics.com [online], "Varactors," Sep. 28, 2009, retrieved on Mar. 19, 2020, retrieved from URL<https://www.electroschematics.com/varactors/>, 2 pages.
Fowler et al., Practical Chemical Sensors from Chemically Derived Graphene, ACS Nano., 3(2):301-306, 2009.
Freedman et al., "Nanopore sensing at ultra-low concentrations using single-molecule dielectrophoretic trapping," Nat Commun., 7:10217, 2016, 9 pages.
Gascoyne et al., "Dielectrophoresis-Based Sample Handling in General-Purpose Programmable Diagnostic Instruments," Proc. IEEE Inst. Electr. Electron Eng., 92(1):22-42, Jan. 2004.
Geiselmann et al., "Three-dimensional optical manipulation of a single electron spin," Nat Nanotechnology., 8:175-179, Mar. 2013.
Giuliodori et al., "Development of a graphene oxide-based assay for the sequence-specific detection of double-stranded DNA molecules," PLoS One, 12(8):e0183952, Aug. 2017, 17 pages.
Grigorenko et al., "Graphene plasmonics," Nature Photonics., 6:749-758, Nov. 2012.
Guo et al., "Development of a Novel Quantum Dots and Graphene Oxide Based FRET Assay for Rapid Detection of invA Gene of *Salmonella*," Front. Microbiol., 8:8, Jan. 2017, 7 pages.
Jose et al., "Individual Template-Stripped Conductive Gold Pyramids for Tip-Enhanced Dielectrophoresis," ACS Photonics., 1:464-470, 2014.
Kakatkar et al., "Detection of DNA and Poly-1-lysine using CVD Graphene-Channel FET Biosensors," Nanotechnology, 26(12): 125502, Mar. 2015, 5 pages.
Kim et al., "Multitarget Dielectrophoresis Activated Cell Sorter," Anal. Chem., 80(22):8656-8661, Nov. 2008.
Kurkina et al., "Label-free electrical biosensing based on electrochemically functionalized carbon nanostructures," Dissertation for the degree of Doctor Rerum Naturalium, Institut fur Anorganische und Analytische Chemie der Justus-Liebig-Universitat Giessen, Feb. 2012, 106 pages.
Kuzyk., "Dielectrophoresis at the nanoscale," Electrophoresis., 32:2307-2313, 2011.
Lee et al., "Optical separation of mechanical strain from charge doping in graphene," Nat. Commun., 3:1024, Aug. 2012, 8 pages.
Li et al., "Graphene-templated supported lipid bilayer nanochannels," Nano Lett., 16:5022-5026, 2016.
Li et al., "Large-Area Synthesis of High-Quality and Uniform Graphene Films on Copper Foils," Science, 324(5932):1312-1314, Jun. 2009.
Liu et al., "Biological and chemical sensors based on graphene materials," Chem. Soc. Rev., 41(6):2283-2307, Mar. 2012.
Loan et al., "Hall Effect Biosensors with Ultraclean Graphene Film for Improved Sensitivity of Label-Free DNA Detection," Biosensors Bioelectronics, 99:85-91, Jan. 2018.
Low and Avouris., "Graphene Plasmonics for Terahertz to Mid-Infrared Applications," ACS Nano., 8(2):1086-1101, 2014.
Low et al., "Polaritons in layered two-dimensional materials," Nature Mater., 16:182-194, Feb. 2017.
Lukacs et al., "Size-dependent DNA Mobility in Cytoplasm and Nucleus," J Biol Chem., 275(3):1625-1629, Jan. 21, 2000.
Ma et al., "Acetone Sensing Using Graphene Quantum Capacitance Varactors," 2016 IEEE Sensors Conference, Orlando, Florida, USA, Oct. 30-Nov. 3, 2016, 3 pages.
Neto et al., "The electronic properties of graphene," Rev Mod Phys., 81:109-162, Jan.-Mar. 2009.
Novoselov et al., "Electric Field Effect in Atomically Thin Carbon Films," Science, 306(5696):666-669, Oct. 2004.
Park et al., "Development of multiplex PCR assay for simultaneous detection of *Salmonella* genus, *Salmonella* subspecies *I. Salm. Enteritidis, Salm. Heidelberg* and *Salm. Typhimuriuni*." J. Appl. Microbiol., 118(1):152-160, Jan. 2015.
Pelton., "Modified spontaneous emission in nanophotonic structures," Nature Photonics., 9:427-435, Jul. 2015.
Ping et al., "Scalable Production of High-Sensitivity, Label-Free DNA Biosensors Based on Back-Gated Graphene Field Effect Transistors," ACS Nano, 10(9):8700-8704, Aug. 2016.

(56) References Cited

OTHER PUBLICATIONS

Regtmeier et al., "Dielectrophoretic Trapping and Polarizability of DNA: The Role of Spatial Conformation," Anal Chem., 82(17):7141-7149, Sep. 1, 2010.

Rodrigo et al., "Mid-infrared plasmonic biosensing with graphene," Science., 349(6244): 165-168, Jul. 10, 2015.

Sanghavi et al., "Electrokinetic Preconcentration and Detection of Neuropeptides at Patterned Graphene-Modified Electrodes in a Nanochannel," Anal. Chemistry, 86(9):4120-4125, May 2014.

Schneider et al., "Tailoring the hydrophobicity of graphene for its use as nanopores for DNA translocation," Nat Commun., 4:2619, 2013, 7 pages.

Sheehan, and L. J. Whitman, "Detection Limits for Nanoscale Biosensors," Nano Lett.. 5(4):803-807, Apr. 2005.

Squires et al., "Making it stick: convection, reaction and diffusion in surface-based biosensors," Nature Biotechnology., 26(4):417-426, Apr. 2008.

UMN.edu [online], "Researchers develop graphene nano 'tweezers' that can grab individual biomolecules," Dec. 4, 2017, retrieved on Jul. 7, 2021, retrieved from URL<https://cse.umn.edu/coilege/news/researchers-develop-graphene-nano-tweezers-can-grab-individual-biomolecules>, 3 pages.

WHO.int [online], "Food safety," available on or before Nov. 21, 2014 via Internet Archive: Wayback Machine URL<https://web.archive.org/web/20141121212113/http://www.who.int/mediacentre/factsheets/fs399/en/>, retrieved on Jul. 7, 2021, retrieved from URL<https://www.who.int/en/news-room/fact-sheets/detail/food-safety>, 6 pages.

Xu et al., "Electrophoretic and Field-Effect Graphene for All-Electrical DNA Array Technology," Nat. Commun, 5:4866, Sep. 2014, 9 pages.

Xu et al., "Nucleic Acid Biosensor Synthesis of an All-in-One Universal Blocking Linker Recombinase Polymerase Amplification with a Peptide Nucleic Acid-Based Lateral Flow Device for Ultrasensitive Detection of Food Pathogens," Anal. Chem., 90(1):708-715, Dec. 2017.

Yan et al., "Damping pathways of mid-infrared plasmons in graphene nanostructures," Nature Photonics., 7:394-399, May 2013.

Zhang et al., "Capacitive sensing of glucose in electrolytes using graphene quantum capacitance varactors," ACS Appl. Mater. Interfaces, 9(44):38863-38869, Oct. 2017.

Zhang et al., "Glucose sensing with graphene varactors," 2016 IEEE Sensors Conference, Orlando, Florida, USA, Oct. 30-Nov. 3, 2016, 3 pages.

Zheng et al., "Manipulating Nanoparticles in Solution with Electrically Contacted Nanotubes Using Dielectrophoresis," Langmuir, 20(20):8612-8619, Sep. 28, 2004.

U.S. Appl. No. 16/972,858, filed Dec. 7, 2020, Steven John Koester, Pending.

\* cited by examiner

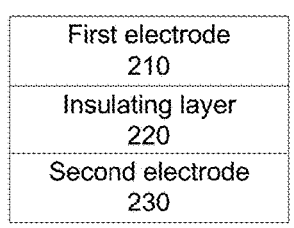
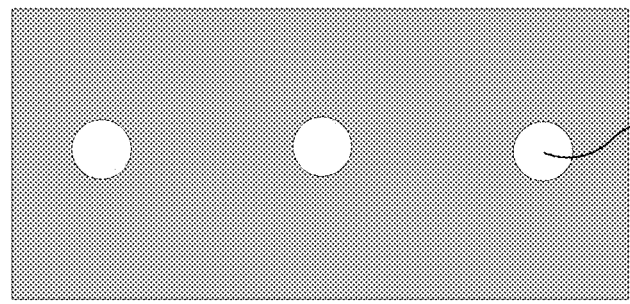
FIG. 2A  FIG. 2B
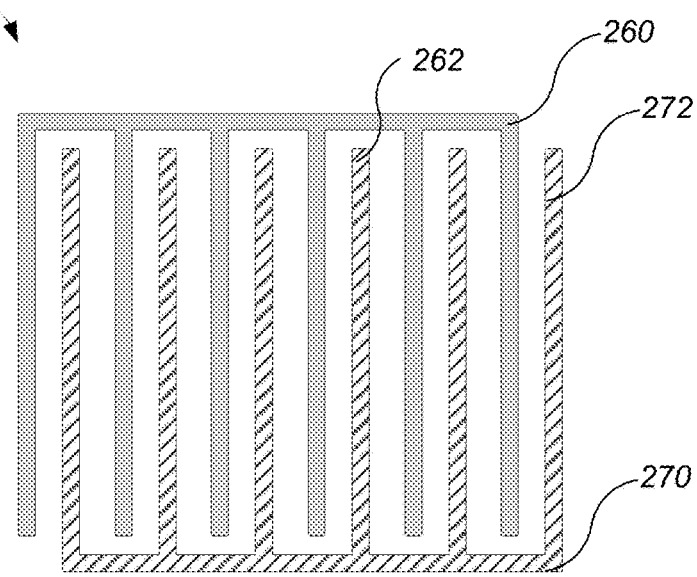
FIG. 2C

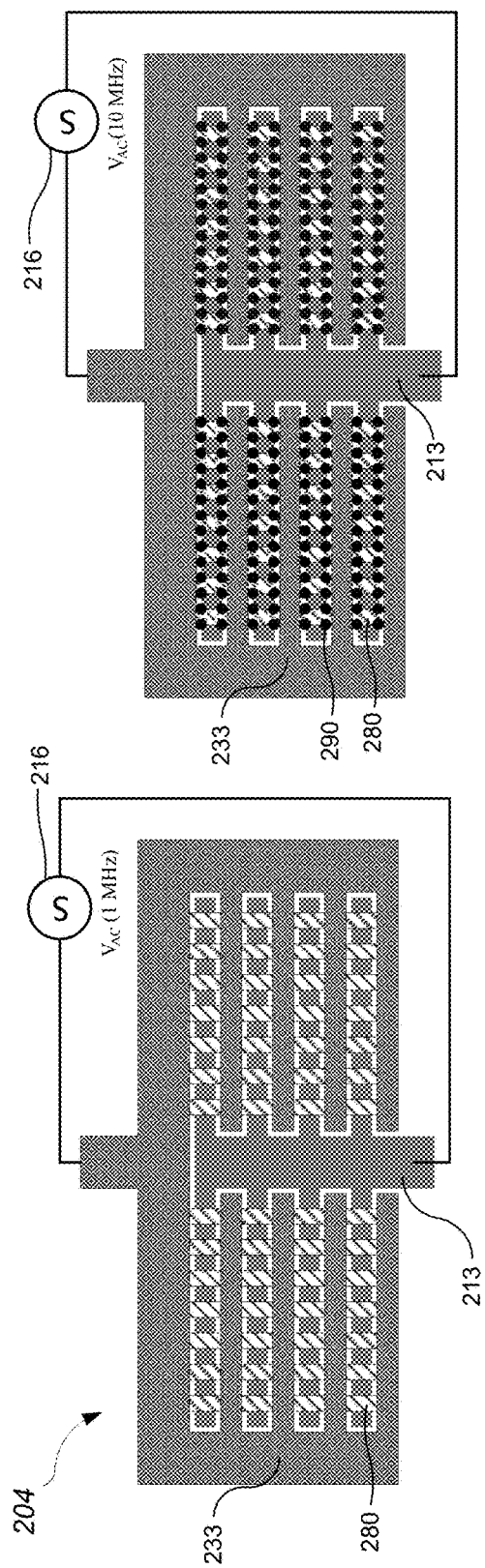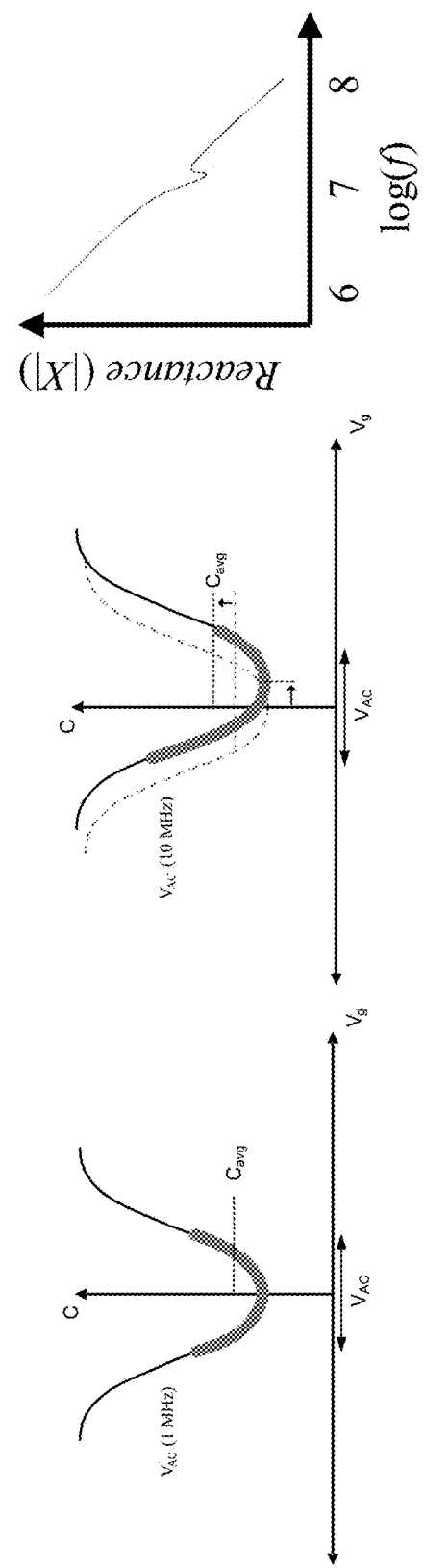
FIG. 2F
FIG. 2H
FIG. 2G
FIG. 2I
FIG. 2J

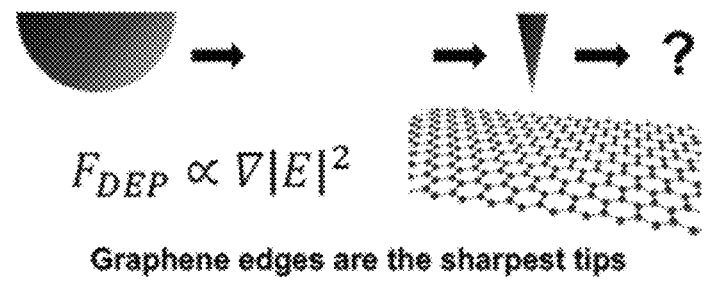
FIG. 3A
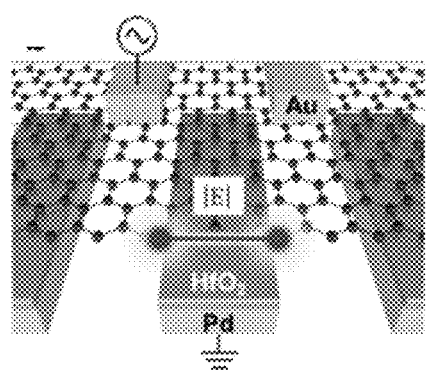 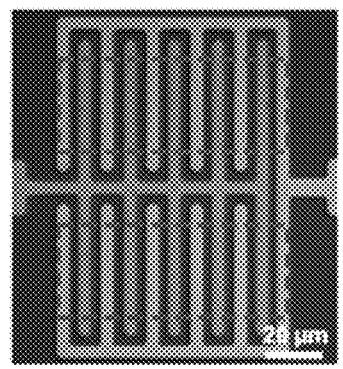 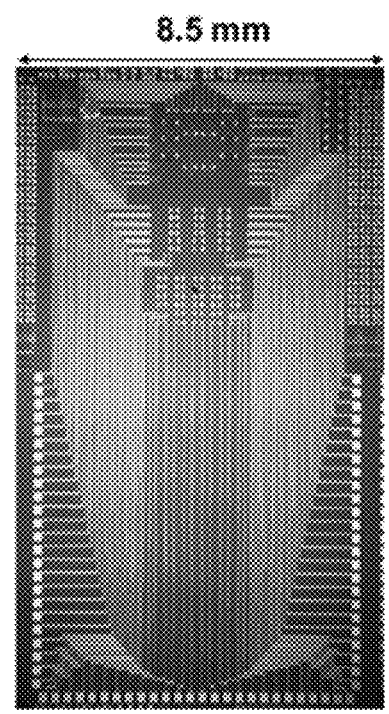
FIG. 3B     FIG. 3C     FIG. 3D

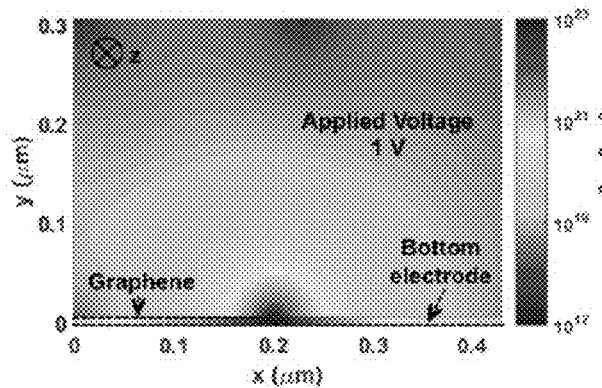 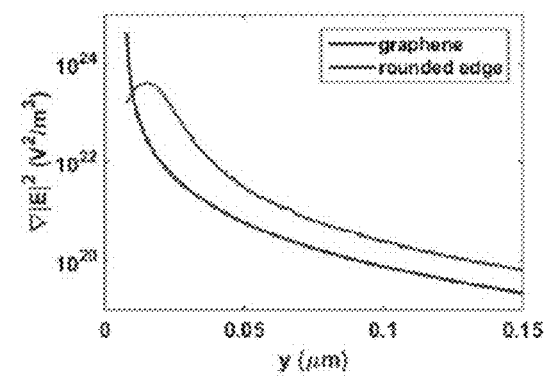
FIG. 4A  FIG. 4B
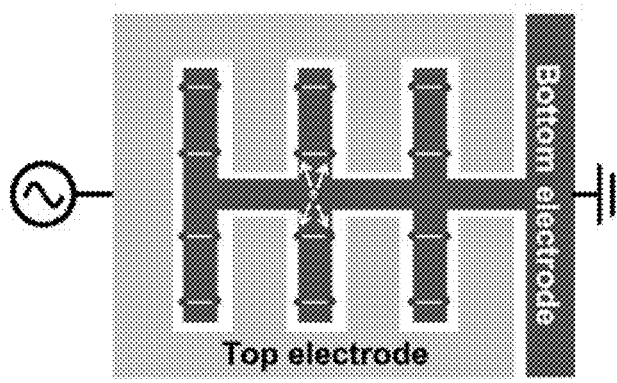 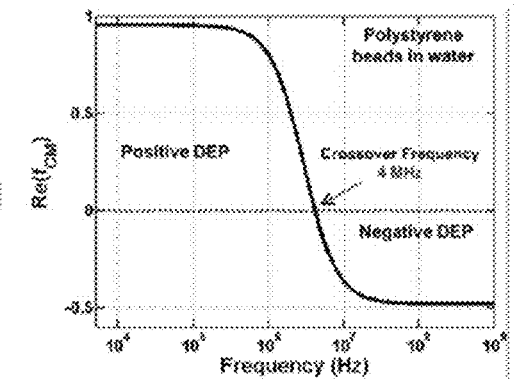
FIG. 5A  FIG. 5B
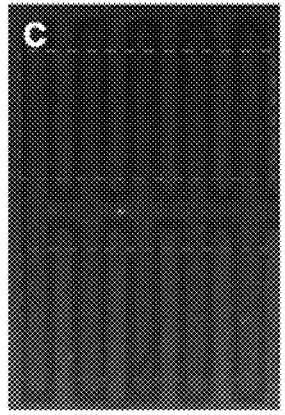 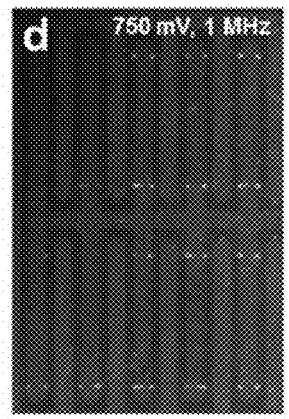 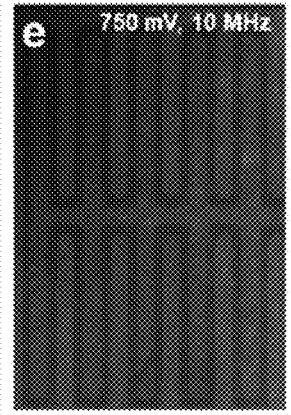 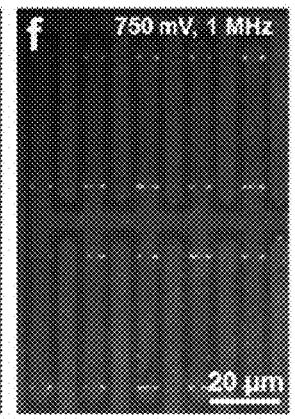
FIG. 5C  FIG. 5D  FIG. 5E  FIG. 5F

ELECTRODES FORMED FROM 2D MATERIALS FOR DIELECTROPHORESIS AND SYSTEMS AND METHODS FOR UTILIZING THE SAME

CROSS-REFERENCE TO RELATED APPLICATIONS

This application is a continuation application of U.S. patent application Ser. No. 16/010,980, filed Jun. 18, 2018 which claims the benefit of U.S. Application Ser. No. 62/521,096, filed on Jun. 16, 2017. The disclosure of the prior application is considered part of the disclosure of this application, and is incorporated in its entirety into this application.

FIELD OF THE INVENTION

This specification relates to devices, systems, and methods for manipulating particles using dielectrophoresis.

BACKGROUND

Dielectrophoresis (DEP) is a technique for manipulating molecules or other polarizable objects (e.g., nanoscale or microscale objects) by using gradient electrical forces obtained from a voltage applied between electrodes.

SUMMARY

This specification relates to devices, systems and methods for manipulating (e.g., separating, trapping, transporting, rotating) particles using DEP using a cell that has an electrode formed from a two-dimensional (2D) material, such as graphene. One or more electrodes formed from a 2D material can provide high electric field gradients, allowing DEP manipulation of particles at voltages significantly lower than electrodes formed from conventional materials.

In general, in one aspect, the invention features a device for applying a dielectrophoretic force on a particle surrounded by a fluid medium, the device including: a cell defining at least one channel for confining the fluid medium; and a first electrode and a second electrode electrically isolated from the first electrode, at least one of the first and second electrodes being formed from a two-dimensional (2D) material providing an atomically sharp edge, wherein the first and second electrodes are arranged sufficiently close to one another and sufficiently close to the channel such that application of a sufficient voltage across the first and second electrode generates an electric field in at least part of channel, the electric field having an electric field gradient sufficient to apply the dielectrophoretic force on the particle in the fluid medium in the channel.

Implementations of the device can include one or more of the following features and/or features of other aspects. For example, the device can include a dielectric layer between the first electrode and the second electrode. In some implementations, the dielectric layer is formed from a dielectric material selected from the group consisting of silicon oxide, hafnium oxide, zirconium oxide, titanium oxide, zinc oxide, boron nitride, aluminum oxide, and silicon nitride. In some implementations, the dielectric layer is formed from an alloy including one or more of oxygen, silicon, hafnium, zirconium, titanium, zinc, boron, nitrogen, or aluminum.

In general, in another aspect, the device features a gap in fluid communication with the channel between the first electrode and the second electrode.

In general, in another aspect, the 2D material can be a variety of materials. Examples of the 2D materials include a non-metal material, graphene, molybdenum disulphide, molybdenum diselenide, molybdenum diteluride, tungsten disulphide, tungsten diselenide, and phosphorene, a single-layer two dimensional (2D) material, and a few-layer two dimensional (2D) material.

In general, in another aspect, the first and second electrodes can be spaced apart by 20 nm or less (e.g., 15 nm or less, 10 nm or less, such as 8 nm, 7 nm, 6 nm, 5 nm, 4 nm, 3 nm, 2 nm).

In general, in another aspect, the sufficient voltage is 5 V or less (e.g., 3 V or less, 2V or less, 1V or less, 750 mV or less, 500 mV or less).

In general, in another aspect, the first and the second electrodes can be configured to form a varactor.

In general, in another aspect, the invention features a voltage source for applying the voltage across the first and second electrodes. In some implementations, the voltage source is an audio output of a smartphone. In some implementations, the voltage source is an on-chip voltage source.

In general, in another aspect, the invention features a pump for pumping the fluid medium through the device.

In general, in another aspect, the invention features an optical imaging device for observing the particle while the voltage source applies the voltage. In some implementations, the optical imaging device is a microscope. In some implementations, the optical imaging device is a camera of the smartphone.

In general, in another aspect, the invention features a method for manipulating a particle surrounded by a fluid medium, the method including: confining the fluid medium to a channel adjacent a first electrode and a second electrode electrically isolated from the first electrode, at least one of the first and second electrodes being formed from a two dimensional (2D) material providing an atomically sharp edge; and applying a voltage to the first and second electrodes while confining the fluid, the voltage being sufficient to generate an electric field in at least part of channel, the electric field having an electric field gradient sufficient to apply a dielectrophoretic force on the particle in the fluid medium in the channel. In some implementations, the dielectrophoretic force applied on the particle in the fluid medium is sufficient to trap the particle.

In some implementations, the method further includes applying a first voltage having a first AC frequency to apply a first dielectrophoretic force sufficient to trap the particle.

In some implementations, the method further includes applying a second voltage having a second AC frequency different from the first AC frequency to apply a second dielectrophoretic force sufficient to release the particle. The second AC frequency can be greater than the first AC frequency. The first and second voltages can be applied to selectively sort the particle based on a type of the particle.

In some implementations, the method further includes determining a capacitance across the first and second electrodes by applying a third voltage. The first voltage and the third voltage can be applied sequentially. The first voltage and the third voltage can be simultaneously applied.

In some implementations, the first electrode is formed from the 2D material and includes a first terminal and a second terminal, and the method further includes determining a resistance of the first electrode by applying a fourth voltage across the first and second terminals of the first electrode.

Among other advantages, implementations of the invention can be used to enable DEP manipulation of particles at relatively low voltages. Use of relatively low voltages can provide for effective DEP particle manipulation without significant heat generation that can accompany higher voltage operation. Low-voltage and low-power operation can enable dense integration of a large number of electrodes on a single chip. Low-voltage operation can enable DEP manipulation of biological cells or molecules without adversely affecting the cells or the molecules. Low power operation can enable portable DEP manipulation devices or systems, e.g., for field-portable bio-sensing. Alternatively, or additionally, particles can be trapped without causing unwanted chemical reactions at the electrode surfaces. Presence of trapped particles can be determined through electrical measurements.

The details of one or more implementations of the subject matter of this disclosure are set forth in the accompanying drawings and the description below. Other features, aspects, and advantages of the subject matter will become apparent from the description, the drawings, and the claims.

DESCRIPTION OF DRAWINGS

FIG. 2A illustrates a schematic cross section of an example of a DEP device.

FIG. 2B illustrates a schematic top view of an example of a DEP device.

FIG. 2C illustrates a schematic top view of an example of a DEP device.

FIGS. 2F-2J illustrates operations of an example of a varactor-integrated DEP device.

FIGS. 3A-3D shows an example of an embodiment of a DEP device.

FIGS. 4A and 4B shows an example of an electrostatics simulation.

FIGS. 5A-5F shows DEP manipulation of 190 nm polystyrene beads using graphene electrodes.

Like reference numbers and designations in the various drawings indicate like elements.

DETAILED DESCRIPTION

Figure 1:
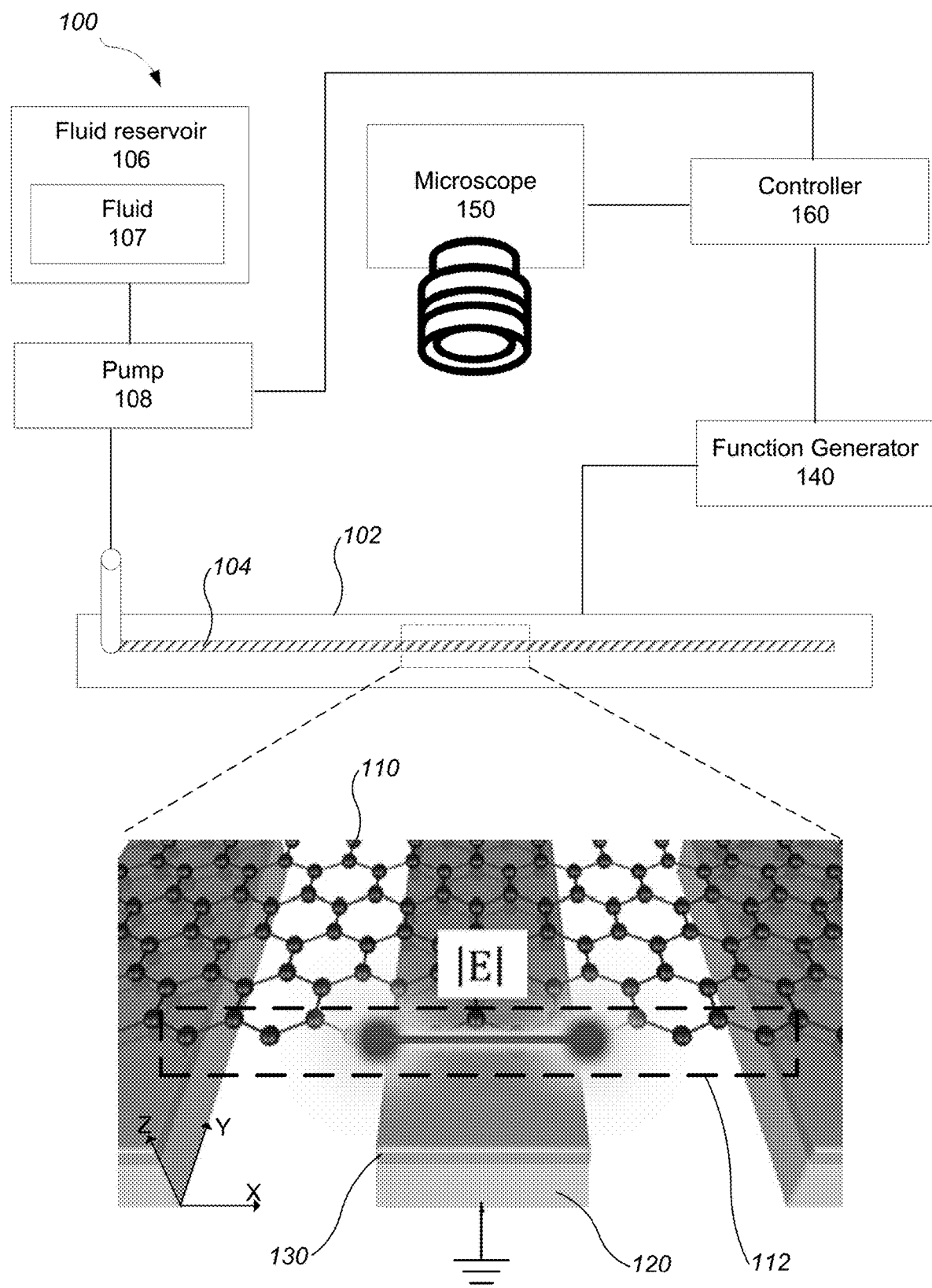
FIG. 1 illustrates a schematic diagram of an embodiment of a system for DEP manipulation of particles.

Referring to FIG. 1, a DEP system 100 includes a DEP cell 102, a fluid channel 104, a fluid reservoir 106, and a pump 108. The DEP system 100 also includes a function generator 140, a microscope 150, and a controller 160 configured to control the DEP system 100.

The fluid reservoir 106 stores a fluid 107 containing particles for DEP manipulation, and a pump 108 can be used to supply the fluid 107 containing the particles to the DEP cell 102 through the fluid channel 104. The fluid channel 104 is in fluid communication with the DEP cell 102, allowing the fluid 107 and the particles contained within to come in close proximity with a surface of the DEP cell 102. For example, the fluid channel 104 can be provided by attaching a PDMS molded cap including a recessed channel to a surface of the DEP cell 102.

The DEP cell 102 includes a first electrode 110, a second electrode 120, and an insulating layer 130. The first electrode 110 is formed from a two dimensional (2D) material, and the first electrode 110 includes an edge 112. The insulating layer 130 electrically isolates the first electrode 110 and the second electrode 120. Applying a time-varying voltage between the first electrode 110 and the second electrode 120 creates a region of strong electric field gradient near the edge 112 of the first electrode, especially at the junction between the edge 112 and the boundary of the second electrode 120 as marked by two dots connected by a line at the edge 112. The strong electric field gradient imparts a DEP force on a nearby particle, and the particle under the influence of the DEP force is driven towards these junctions, or "trapping sites." As an example, an electric field gradient sufficient for attracting or trapping particles typically falls in a range between $10^{22}$ to $10^{24}$ $v^2/m^2$.

The controller 160 controls the DEP manipulation of particles by controlling the function generator 140 and the pump 108, and by analyzing data provided by the microscope 150. A typical operation of the DEP system 100 includes trapping of particles on the DEP cell 102. In such an operation, the controller 160 controls the pump 108 to supply the fluid 107 containing the particles for DEP manipulation.

The controller 160 controls the function generator 140 to apply a time-varying voltage between the electrodes 110 and 120. The time-varying voltage can have controllable parameters, including a peak-to-peak amplitude, a DC offset voltage and a frequency. The parameters of the voltage can be changed to change the generated DEP force. While a function generator 140 is illustrated, in general, any voltage source capable of generating an AC voltage may be used to apply the time-varying voltage between the electrodes 110 and 120.

The controller 160 acquires a series of images from the microscope 150. The microscope 150 captures images of the trapping sites (e.g., the edge 112) to be analyzed by the controller 160 for presence of trapped particles. The microscope 150 can be a fluorescence microscope, which illuminates the trapped particle with an excitation source to induce fluorescence emission from the trapped particle.

The controller 160 analyzes the series of images from the microscope 150 to determine presence of trapped particles. If sufficient trapped particles are detected, the controller 160 can stop the fluid flow by turning off the pump 108, and maintain the trapping force by continued application of the time-varying voltage by the function generator 140. If sufficient trapped particles are not detected, the controller 160 can change the properties of the applied time-varying voltage to change the DEP force to potentially increase the number of trapped particles.

The controller 160 can release the trapped particles by changing the properties of the applied time-varying voltage applied by the function generator 140. For example, the amplitude of the applied voltage can be reduced, or the frequency can be increased or decreased to change the direction of the generated DEP force.

In some implementations, a camera of a mobile device can be used for acquiring images of the trapping sites. One or more lenses can be arranged to provide a magnification to the camera of the mobile device. In some implementations, an output port (e.g., audio port or charging port) of the mobile device can be used to apply the time-varying voltage between the electrodes 110 and 120. The mobile device can be used as the controller 160 to control the DEP system 100. Examples of the mobile device include a smartphone and a tablet.

Forming the first electrode 110 from a 2D material can greatly enhance the generated DEP force. Two dimensional (2D) materials are typically crystalline materials that are very thin in at least one direction, having one or more atomic layers in that direction. For example, the edge 112 of the first electrode 110 formed from a 2D material can be one atom thick, providing an atomically sharp edge. Therefore, the exposed edges of a single-layer 2D material can function as atomically sharp 'lightning rods', generating an ultrahigh-gradient of electric fields.

Generally, a 2D material can be classified as a monolayer or few-layer 2D material. For example, in some cases, a 2D material is only a single atomic layer thick ("monolayer"). In certain cases, a 2D material is more than one atomic layer thick ("few-layer," e.g., up to 10's of atomic layers).

In general, 2D materials can be single-crystalline or polycrystalline. A single-crystalline 2D material consists of a single, continuous crystalline domain. A polycrystalline 2D material can have two or more crystalline domains separates by grain boundaries. The two or more crystalline domains can have different crystalline lattice orientations. A polycrystalline 2D material can have a thickness similar to the single-crystalline 2D material.

Generally, the thickness of a layer of a 2D material varies depending on its atomic composition, ranging between 0.3 nm to 20 nm. Examples of thin 2D materials include single-layer graphene which has a thickness on the order of 0.3 nm, single-layer phosphorene which has a thickness of 0.55 nm and single-layer MoS$_2$ which has a thickness of 0.65 nm.

In some cases, at least in part, 2D materials can have more than one layer of atoms. Such a material general includes two or more layers ("few-layer") of atoms stacked on top, e.g., along the Z axis of FIG. 1. The number of layers of the few-layer 2D material can vary, from 2 layers to 10's of layers. The edge 112 provided by a few-layer 2D material is atomically sharp, with a thickness of 2-10's of atoms.

The 2D material should have sufficiently high electrical conductivity to enable efficient generation of the electric field gradient. Having sufficiently high electrical conductivity prevents excessive voltage drop across an electrode, which can decrease the generated electric field gradient. Having sufficiently high electrical conductivity also reduces heat generation through resistive heating. Having high carrier mobility improves conductivity at a given electron or hole carrier density.

In general, a variety of 2D materials can be used for the electrodes in the DEP cell 102 of the DEP system 100. For example, the first electrode 110 can be formed using a first 2D material, and the second electrode 120 can be formed using a second, different 2D material. As another example, the first electrode 110 can be formed using a 2D material, and the second electrode 120 can be formed using conductive metals or alloys.

Examples of 2D materials include graphene, molybdenum disulphide, molybdenum diselenide, molybdenum ditelluride, tungsten disulphide, tungsten diselenide, and phosphorene.

Graphene can be a suitable alternative to noble metals for constructing sensors due to its electrical tunability, high quantum efficiency for light-matter interactions and tightly confined mid-infrared plasmons. Unlike noble metals such as gold or silver, doping in graphene can be electrical tuned, giving a new degree of freedom to probe biomolecules. Nano-patterned graphene such as ribbons, nano-channels, or nano-pores can be used for bio-sensing to achieve high sensitivity.

The second electrode 120 is electrically isolated from the first electrode 110 so that a potential difference applied across the two electrodes generates an electric field between them.

The second electrode 120 can be formed using various conductive materials, such as, for example, electrically conductive 2D materials (e.g., those described above), or electrically conductive metals, silicides, or alloys, such as Gold, Palladium, Platinum, Tungsten, Aluminum, Copper, Molybdenum, Iridium, or alloys or silicides of such metals.

The insulating layer 130 is formed from a dielectric material. Examples of dielectric materials include hafnium dioxide, zirconium oxide, silicon dioxide, aluminum oxide, hexagonal boron nitride, silicon nitride, and insulating 2D materials. As another example, the dielectric layer can be from an alloy including one or more of oxygen, silicon, hafnium, zirconium, titanium, zinc, boron, nitrogen, or aluminum. The thickness of the insulating layer 130 affects the magnitude of the established electric field, where a low thickness increases the electric field strength. In some implementations, a range of thickness of the insulating layer 130 can include 1-20 nm, e.g., 8 nm.

In general, oxides include compounds of oxygen and another element having various ratios, including dioxides having two oxygen atoms. Further, the various oxides can have non-integral composition ratios. For example, dioxides can be non-stoichiometric dioxides that have non-integral ratios of the constituent elements (e.g., a non-stoichiometric silicon dioxide may have 2.1 oxygen atoms for every 1 silicon atom).

In some embodiments, the insulating layer 130 is a liquid. In this case, the fluid channel 104 is formed between the first electrode 110 and the second electrode 120. The fluid 107 containing the particles to be trapped can flow between the first electrode 110 and the second electrode 120, supplying the particles for trapping.

Without wishing to be bound by theory, it is possible to calculate the gradient of the electric field intensity ($\nabla |E|^2$), which is responsible for DEP trapping, for a semi-infinite graphene "electrode" electrically biased by a metal gate electrode, as shown in FIG. 4a. Here, it is noted that graphene is not a perfect metal, due to its relatively small electronic density-of-states. The electrostatics problem then requires a self-consistent solution of Poisson's equation and that of the finite charge density within graphene, as imposed by its Dirac-like energy dispersion. The electrostatic potential φ(x, y) is obtained by solving the 2D Poisson equation $$\nabla \cdot (\varepsilon \nabla \varphi) = en\delta(y-y_0) \quad (3)$$

self-consistently with the net electron concentration (per unit area) on the graphene layer.

$$n(x) = \frac{2}{\pi}\left(\frac{k_B T_R}{\hbar v_F}\right)^2\left[F_1\left(\frac{\mu}{k_B T_R}\right) - F_1\left(\frac{-\mu}{k_B T_R}\right)\right], x < 200 \text{ nm} \quad (4)$$

The symbols are defined as follows: $\varepsilon = \varepsilon_r \varepsilon_0$ ($\varepsilon_r$ is the dielectric constant of the different media and $\varepsilon_0$ the vacuum permittivity), δ is Dirac's delta function, $y_0 = 8$ nm the vertical position of the graphene layer, ℏ the reduced Planck constant, $v_F \approx 10^6$ m/s the graphene Fermi velocity, $F_1$ the Fermi-Dirac integral of order 1, and μ(x) the position-dependent chemical potential. The latter, in turn, is computed as $$\mu(x) = e\varphi(x, y = y_0), x < 200 \text{ nm} \quad (5)$$

The Dirichlet boundary condition φ=$V_g$=1 V was applied at the bottom edge of the simulation domain and Neumann boundary conditions everywhere else. The gradient of $|E|^2$ is computed from φ with finite differences.

An 8-nm-thick $HfO_2$ layer with a dielectric constant of 25 was assumed between the electrodes. The rest of the simulation domain was assumed to be water with a dielectric constant of 80. The bottom electrode was treated as an ideal metal and graphene was modeled as a layer with zero thickness. The $\nabla|E|^2$ field gradient map is shown in FIG. 4a for a 1 V DC bias applied between the gate and graphene electrodes. The $\nabla|E|^2$ value is highest at the edge of the graphene electrode, which acts as a hotspot for DEP trapping. A vertical cut-line of the $\nabla|E|^2$ field gradient at the position of the graphene edge is plotted and compared to a case where the graphene electrode was replaced with a realistic metal electrode of 20 nm thickness and 10 nm radius of curvature (FIG. 4b). The maximum value of $\nabla|E|^2$ at the graphene edge is about an order of magnitude higher as compared to the metal electrode. However, the effect of the graphene edge becomes less pronounced away from the boundary. In the bulk solution (away from the electrode boundary), the effect of DEP is similar in both cases and mostly dependent on the gap between the electrodes (8 nm here). Even then, for ultrasmall particles such as proteins or quantum dots that are typically <10 nm in diameter, graphene electrodes could provide a stronger trapping force to hold them on to the electrode edge.

The time-averaged DEP force on a particle of radius R and in a medium of permittivity $\varepsilon_m$ is expressed as $$\vec{F}_{DEP}(\omega) = \pi \varepsilon_m R^3 \cdot \text{Re}\left(\frac{\varepsilon_p^*(\omega) - \varepsilon_m^*(\omega)}{\varepsilon_p^*(\omega) + 2\varepsilon_m^*(\omega)}\right) \nabla |E|^2 \quad (8)$$

where $|E|$ is the magnitude of the electric field, $\varepsilon_p^*(\omega)$ and $\varepsilon_m^*(\omega)$ are the complex permittivities of the particle and the medium, respectively. DEP force depends on the particle volume that goes down with the particle size. However, the thermal Brownian motion becomes very important as the particle size is reduced to sub-micron length scale.

To trap a particle, it is required to overcome the thermal force, $F_T$, given by $$F_T = \frac{k_B T_R}{2R} \quad (2)$$

Since DEP force is proportional to the field gradient term $\nabla|E|^2$, reducing the radius of curvature of electrode features (e.g. tips or edges) or electrode-to-electrode separation can boost its magnitude. Atomically thick graphene can be used to reduce the radius of curvature of electrode features, as shown in FIG. 3A.

A DEP device can have various geometrical configurations of the first and the second electrodes. In general, the electrode geometry should provide an appropriate electric field gradient in the channel in which the particles flow to allow for DEP manipulation. Referring to FIGS. 2A and 2B, a DEP device 200 can have pores for trapping particles. Referring to FIG. 2A, the DEP device 200 can have a cross-section consisting of a first electrode 210 at top, an insulating layer 220, and a second electrode 220 at the bottom in a stacked configuration. Referring the FIG. 2B, the DEP device 200 includes pores 240. The pores 240 can be etched holes through the cross-section of FIG. 2A. The exposed edges of the first electrode 210 and/or the second electrode 230 creates a region of strong electric field gradient, creating trapping sites at the pores 240. The first electrode 210 can be formed from 2D materials, and the second electrode 230 can be formed from various conductive materials, such as, for example, electrically conductive 2D materials (e.g., those described above), or electrically conductive metals or alloys, such as Gold, Palladium, Platinum, Tungsten, Aluminum, Copper, Molybdenum, Iridium, or alloys or silicides of such metals. The insulating layer 220 is formed from a dielectric material. Examples of dielectric materials include hafnium dioxide, zirconium oxide, silicon dioxide, aluminum oxide, hexagonal boron nitride, silicon nitride, insulating 2D materials, and alloys of such materials. The thickness of the insulating layer 220 affects the magnitude of the established electric field, where a low thickness increases the electric field strength. In some implementations, a range of thickness of the insulating layer 220 can include 1-20 nm, e.g., 8 nm.

Referring to FIG. 2C, a DEP device 201 includes a first electrode 260 and a second electrode 270. The first electrode 260 includes fingers 262 and the second electrodes 270 includes fingers 272. The first electrode 260 and the second electrode 270 are positioned such that finger 262 and 272 alternate as shown. The edges of the fingers 262 and 272 creates a region of strong electric field gradient, creating trapping sites along the fingers. The first electrode 260 can be formed from 2D materials, and the second electrode 270 can be formed from various conductive materials, such as, for example, electrically conductive 2D materials (e.g., those described above), or electrically conductive metals, silicides, or alloys, such as Gold, Palladium, Platinum, Tungsten, Aluminum, or Copper.

In some embodiments, the first electrode 260 and the second electrode 270 are vertically separated by a distance of 1 nm to 50 nm, and a channel is formed by the separation. The channel can be configured to provide a flow of a liquid containing particles to be trapped.

While electrodes 260 and 270 with multiple fingers have been illustrated, in general, the first and second electrodes 260 and 270 can each have varying number of fingers. For example, the first electrode 260 and the second electrode 270 can each have a single finger. As another example, the first electrode 260 and the second electrode 270 can have different number of fingers.

While the fingers 262 and 272 of the electrodes 260 and 270 are arranged in parallel in FIG. 2C, in general, the fingers can be in various relative orientations. For example, the first and second fingers can be oriented perpendicular to each other, resulting in multiple crossings between the fingers.

Figure 2D:
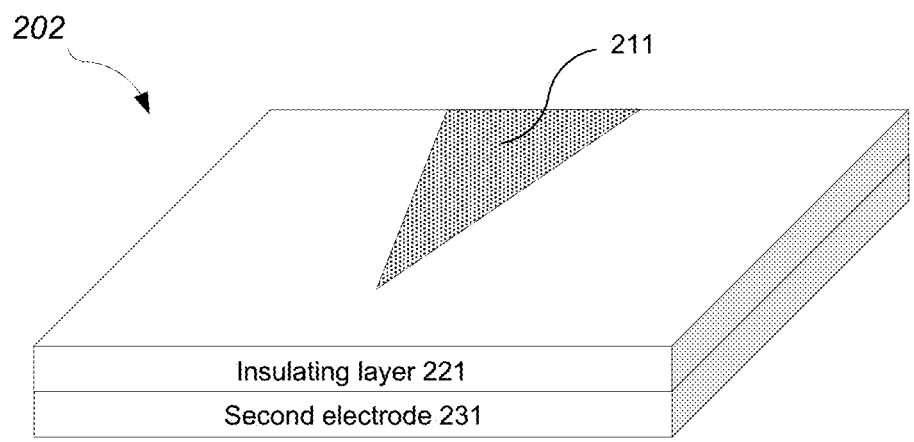
FIGS. 2D-2E illustrate schematic perspective views of examples of a DEP device.

Referring to FIG. 2D, a DEP device 202 includes a first electrode 211, an insulating layer 221, and a second electrode 231. The first electrode 211 can be formed from 2D materials, and the second electrode 231 can be formed from various conductive materials, such as, for example, electrically conductive 2D materials (e.g., those described above), or electrically conductive metals or alloys, such as Gold, Palladium, Platinum, Tungsten, Iridium, Molybdenum, Aluminum, or Copper. The insulating layer 221 may be similar to the insulating layer 220 of FIG. 2A. In this embodiment, the first electrode 211 is shaped to form a tapered tip. The tapered tip can lead to generation of high electric field gradient, creating a trapping site near the tapered tip.

Figure 2E:
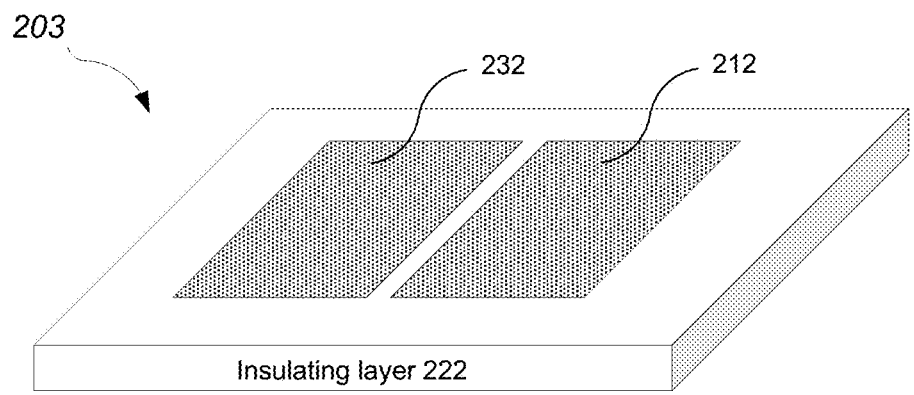

Referring to FIG. 2E, a DEP device 203 includes a first electrode 212, an insulating layer 222, and a second electrode 232. The first and second electrodes 212 and 232 can be formed from 2D materials. The insulating layer 222 may be similar to the insulating layer 220 of FIG. 2A. In this embodiment, the first electrode 212 and the second electrode 232 are separated by a slit. The slit, for example, can be defined using a combination of photolithography and etching. Edges of the first and second electrodes 212 and 232 can lead to generation of high electric field gradient, creating a line of trapping sites across the slit.

While the foregoing description of DEP system 100 includes a microscope for performing optical detection of trapping of the particles, other detection schemes can be used. For example, electrical detection can be used. Referring to FIGS. 2F-2J, operations of an example of a varactor-integrated DEP device 204 are illustrated. FIG. 2F shows a top view of a graphene varactor-integrated DEP device 204. The DEP device 204 includes a first fingered electrode 213, a second fingered electrode 233, and a graphene electrode 280. The graphene electrode 280 is electrically coupled to the second fingered electrode 233. The graphene electrode 280 has been subdivided into several smaller fingers to increase the number of edges and crossings of the graphene electrode 280 over the first finger electrode 213, where particles can be trapped. For example, the width of the subdivided fingers can range from 100 nm to 5 μm.

The graphene electrode 280 is electrically isolated from the first fingered electrode 213. For example, an insulating layer similar to the insulating layer 130 may be arranged between the first fingered electrode 213 and the graphene electrode 280. As such, an example stack-up of the DEP device 204 may include, in the order as listed, the first fingered electrode 213, the insulating layer, the graphene electrode 280, and the second fingered electrode 233. Further, other layers of materials may be present between the first fingered electrode 213, the insulating layer, and the graphene electrode 280.

The first and second fingered electrodes 213 and 233 may be formed from various conductive materials. Examples of conductive materials include metals, silicides, or alloys, such as Gold, Palladium, Platinum, Tungsten, Chromium, Titanium, Iridium, Molybdenum, Aluminum, or Copper. In some implementations, different layers of conductive materials can be stacked to form the first and second electrodes 213 and 233. Such stacking may be beneficial for improving adhesion between the metal and the insulating layer or the graphene, and for improving the quality of electrical contact to the graphene electrode 280.

Initially, an AC bias is applied between a the first fingered electrode 213 ("gate electrode") and the second fingered electrode 233 coupled to the graphene electrode 280 at a frequency that does not correspond to DEP trapping (e.g., 1 MHz) for a particular type of particles, and no particles are trapped as a result. The AC bias can be applied through a voltage source 216. Referring to FIG. 2G, a capacitance of the varactor-integrated DEP device 204 as a function of gate voltage is shown. FIG. 2G shows an example of a measured capacitance as a function of DC gate voltage $V_g$ of the device 204 in absence of trapped particles. Variation of the measured capacitance across the AC bias voltage ($V_{ac}$) used for performing DEP experiment is indicated by the bolded portion of the capacitance curve. Without wishing to be bound by theory, the device 204 has a voltage-dependence capacitance due to a quantum capacitance effect. As such, for a given excitation voltage $V_{ac}$, the capacitance of the DEP device 204 changes over a period of the AC bias voltage, and the average measured capacitance ($C_{avg}$) value is indicated by the dashed line.

Referring to FIG. 2H, the frequency of the applied AC bias is changed to a frequency that corresponds to DEP trapping (e.g., 10 MHz) for the particular type of particles.

As a result, particles 290 are trapped along the edges of the graphene electrode 280. The fingered geometry of the DEP device 204 increases the percentage of an active area of the DEP device 204 for trapping particles. Referring to FIG. 2I, an example of a change in measured capacitance in presence of trapped particles is shown. Without wishing to be bound by theory, a shift in the capacitance curve (e.g., in the $+V_g$ direction) can be induced due to an electrostatic interaction of the trapped particles 290 with the graphene electrode 280. This shift can cause a change in the measured average capacitance $C_{avg}$ as indicated by an upward arrow. This change in measured average capacitance induced by the presence or absence of the particles 290 can be used to electrically detect trapping of particles.

In some implementations, a DC bias can be applied across the gate electrode 213 and the second fingered electrode 233 in addition to the AC bias. The DC bias can be used, for example, to shift the capacitance curve.

Referring to FIG. 2J, an example of a change in the measured reactance of the DEP device 204 as a function of frequency is shown. For example, a dip in the reactance at frequencies coinciding with the trapping frequency for a particular type of particles can be used to electrically detect trapping of particles. In addition, other features in the reactance vs. frequency, such as a peak, may also be utilized to detect trapping of particles.

Various types of electrical readout methods may be used to readout presence of the particles 290 from the DEP device 204. For example, a time-multiplexed approach can be used in which the DEP device 204 is operated to repeatedly switch between a trapping mode and a measurement mode. The time-multiplexed approach may be advantageous in that a simple circuit dedicated for generating a trapping voltage can be used in combination with another standard circuit used for measuring capacitance of a device. Further, the time-multiplexing allows the capacitance to be measured at a frequency and a voltage different from the trapping voltage, which can provide additional flexibility in the operation of the DEP device 204.

Example operation of the time-multiplexed operation is provided. During the trapping mode, a time varying voltage sufficiently large (e.g., 5 V) to trap the particles is applied. The operation mode of the DEP device 204 can then be switched to the measurement mode, during which the capacitance of the DEP device 204 is measured. Capacitance of the DEP device 204 can be measured, for example, by applying an AC voltage and measuring a corresponding AC current. In some implementations, the trapping voltage and the measurement voltage can be generated and switched by a single circuit, such as the voltage source 216. In some implementations, the trapping voltage and the measurement voltage can be generated by separate circuits, and be switched by a switching circuit under control of, for example, the controller 160 of FIG. 1. Due to mechanical inertia of the trapped particles 290, the particles may remain effectively stationary in the timescale of the measurement duration. For example, the measurement can be made in less than, for example, 10 μs, 100 μs, or 1 ms. Once the measurement is complete, the operation can be switched back to the trapping mode to maintain trapping of the particles 290.

Another example of an electrical readout approach of the DEP device 204 is frequency-multiplexed approach. In the frequency-multiplexed approach, the trapping voltage is set at a first frequency, and a measurement voltage is set at a second frequency different from the first frequency. The trapping voltage and the measurement voltage at different frequencies can be generated, for example, by separate sources and be multiplexed to be simultaneously supplied to the DEP device 204. By measuring a flow of current at the measurement voltage source, the reactance of the DEP device 204 can be determined. As another example, a lock-in detection technique can be used to determine the capacitance of the DEP device 204 while a trapping voltage is being applied. The frequency-multiplexed approach can provide robust particle trapping capability as the trapping force on the particles 290 are maintained without interruptions.

In general, the readout operations can be controlled by the controller, such as the controller 160 of FIG. 1.

While the DEP device 204 with graphene electrode 280 is described, in general, the graphene electrode 280 may be substituted with a 2D material electrode formed from 2D materials.

Figure 2K:
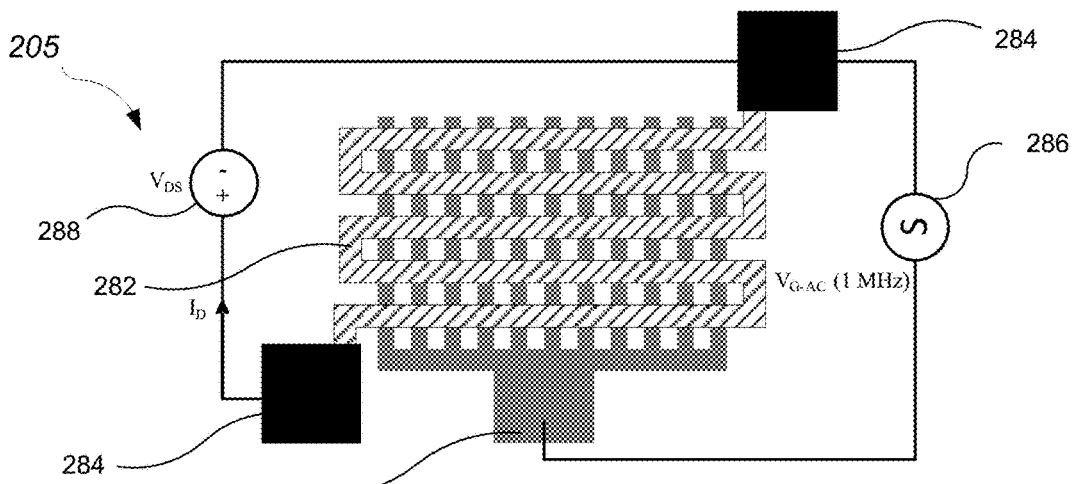
FIGS. 2K-2M illustrates operations of an example of a FET-integrated DEP device.
Figure 2L:
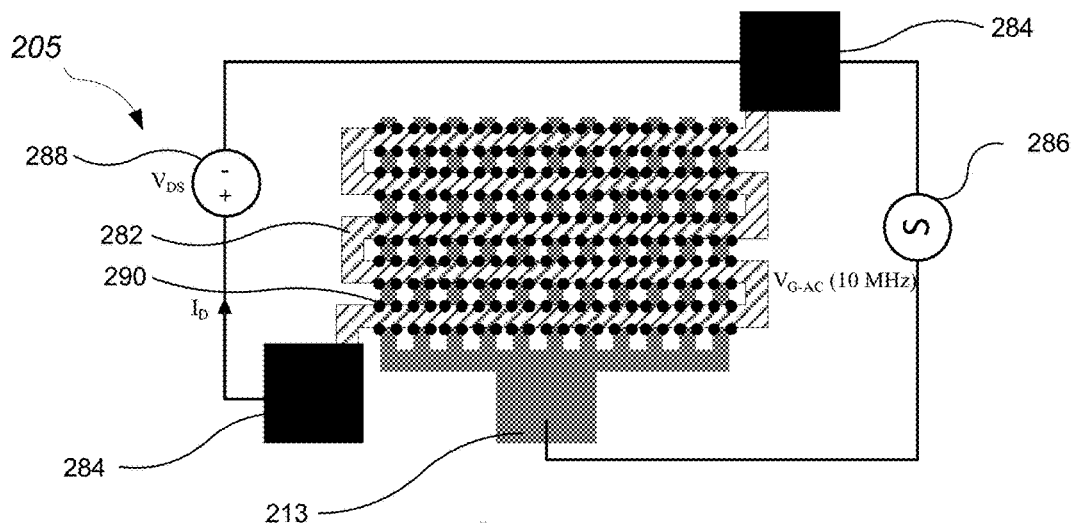
Figure 2M:
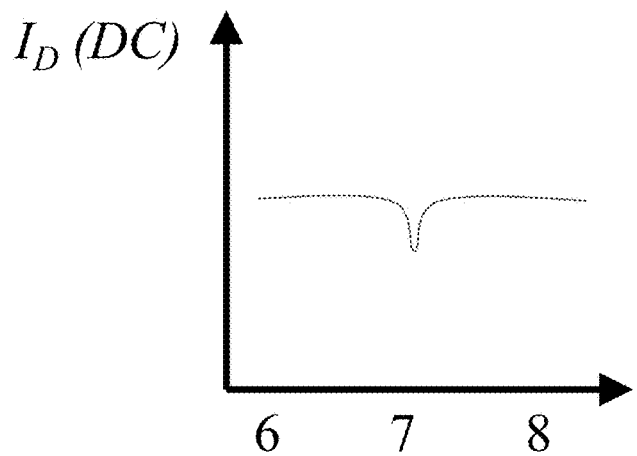

Referring to FIGS. 2K-2M, operations of an example of a field effect transistor (FET)-integrated DEP device 205 are illustrated. FIG. 2K shows a graphene FET-integrated DEP device 205 that includes the first fingered electrode 213, a graphene electrode 282, and contacts 284. The contacts 284 are electrically coupled to the graphene electrode 282. The DEP device 205 is a three-terminal device, in which the first fingered electrode 213 serves as a gate electrode, and the two contacts 284 serves as the source and drain terminals. The graphene electrode 282 is arranged in a serpentine shape to increase crossing sites with the first fingered electrode 213. Increasing the crossing sites leads to increased number of edges where particles can be trapped. For example, widths of the serpentine strips of the graphene electrode 280 can range from 100 nm to 5 μm, and widths of the fingers of the first fingered electrode 213 can range from 0.1 μm to 5 μm.

The graphene electrode 282 is electrically isolated from the first fingered electrode 213. For example, an insulating layer similar to the insulating layer 130 may be arranged between the first fingered electrode 213 and the graphene electrode 282. As such, an example stack-up of the DEP device 205 may include, in the order as listed, the first fingered electrode 213, the insulating layer, and the graphene electrode 282. The insulating layer may act as the "gate oxide" of the 3 terminal FET device formed by the graphene electrode 282 and the first fingered electrode 213.

The contacts 284 may be formed from various conductive materials. Examples of conductive materials include metals, silicides, or alloys, such as Gold, Palladium, Platinum, Tungsten, Chromium, Titanium, Iridium, Molybdenum, Aluminum, or Copper. In some implementations, different layers of conductive materials can be stacked to form the contacts 284.

The DEP device 205 can be electrically measured by applying a DC voltage, an AC voltage, or both (collectively referred to as "measurement voltage") between the two ends of the graphene electrode 282 through the contacts 284, and measuring the resulting drain current ($I_D$) while applying an AC voltage ("trapping voltage") between the first fingered electrode 213 ("gate electrode") and the graphene electrode 282 to induce DEP trapping. The trapping voltage can be applied through a voltage source 286 and the measurement voltage can be applied through a source meter 288 configured to apply a voltage and measure corresponding current. Initially, a trapping voltage is applied between the gate electrode 213 and the graphene electrode 282 at a frequency that does not correspond to DEP trapping (e.g., 1 MHz) for a particular type of particles, and no particles are trapped.

The measurement voltage is typically smaller than the trapping voltage to mitigate a voltage drop across the two terminals of the graphene electrode 284 caused by the flow of the drain current $I_D$. For example, the measurement voltage can be 10 to 100 times smaller than the amplitude of the trapping voltage.

In some implementations, the trapping voltage can have a DC bias in addition to the AC voltage. The DC bias can be used, for example, to bias the graphene electrode 282 to control its conductivity.

Referring to FIG. 2L, the frequency of the applied trapping voltage is changed to a frequency that correspond to DEP trapping (e.g., 10 MHz) for the particular type of particles. As a result, the trapped particles 290 are trapped at the edges of the graphene electrode 282.

While an example trapping operation where particles are trapped by increasing the frequency of the trapping voltage is described, in general, the frequency of the trapping voltage can initially be set to be higher than the trapping frequency, then be lowered to induce the trapping. Further, once the particles 290 have been trapped, the particles 290 can be released by changing the frequency away from the trapping frequency.

While a serpentine graphene electrode 282 is illustrated, in general, the graphene electrode 290 can be designed to have various shapes. For example, the graphene electrode 290 can be a straight electrode making a single pass over the fingers of the gate electrode 213.

Referring to FIG. 2M, an example of a change in measured drain current in presence of trapped particles is illustrated. For example, the presence of the trapped particles 290 can cause a reduction or an increase in the flow of the drain current $I_D$ for a given voltage across the two contacts 284 of the graphene electrode 282. Without wishing to be bound by theory, such a reduction or an increase in the drain current may be a result of a shift of the Dirac voltage to more positive or negative values as a result of the trapped particles 290 and associated electrostatic interactions of the particles 290 with the graphene electrode 282. The trapped particles may increase or decrease the conductivity of the graphene electrode 282 through carrier scattering or electrostatic screening phenomenon within the graphene. In the case where the trapped particles 290 causes a reduction in conductivity, the reduction in $I_D$ manifests as a dip in the measured drain current $I_D$ when the applied trapping voltage is at frequencies coinciding with the trapping frequency for a particular type of particles. As such, measurement of the drain current $I_D$ of the DEP device 205 can be used to electrically detect trapping of particles.

DEP device 205 allows simultaneous trapping and measurement due to the presence of the three device terminals. Additionally, presence of the three terminals allow the trapping voltage and the measurement voltage to be applied independent of one another. Further, measurement circuitry for measuring DC current may be simpler than AC current measurement circuitry. The serpentine field effect transistor geometry may improve sensitivity of trapped particle detection, as the changes in conductivity contributed by each of the trapped particles 290 provide a cumulative change in the measured drain current $I_D$.

While the DEP device 205 with graphene electrode 282 is described, in general, the graphene electrode 282 may be substituted with a 2D material electrode formed from 2D materials.

The described DEP devices such as devices 200 through 205 may be interfaced with fluids containing particles to be trapped in various ways. For example, the DEP devices can be integrated into the DEP cell 102 of FIG. 1 such that the 2D material electrodes comes in contact with the fluid 107. As another example, droplets of fluid may be dispensed directly onto the DEP devices 200 through 205. The DEP devices may be one-time use devices that can be easily swapped between different trapping experiments.

In general, a variety of methods can be used to make DEP devices that utilize 2D materials. For example, 2D materials can be deposited by chemical vapor deposition (CVD). The 2D material can be grown by CVD directly on the final substrate or grown on a separate substrate and then be transferred to the final device substrate. For example, graphene can be grown on copper by CVD, and then be transferred onto the final substrate by removing the copper using a selective etch. Once 2D materials are deposited, standard planar processing techniques for integrated circuit fabrication can be used to make the DEP device. The deposited 2D materials can be masked using photolithography, and patterned using plasma etching. The insulating layer can be deposited using atomic layer deposition, evaporation, sputtering, plasma-enhanced CVD, or a film transfer method (e.g., for transferring an insulating 2D material). Metal electrodes can be deposited using sputtering, evaporation, or electroplating.

A particular embodiment of the disclosed DEP device, such as the DEP device illustrated in FIG. 3B, can be made by the following steps. First, a metal electrode (Pd) pattern is created on a Si wafer with a thick layer of $SiO_2$ on it. Next, the entire wafer surface, including the Pd electrode, is coated with 8-nm of $HfO_2$ deposited by atomic layer deposition (ALD). Then, single-layer graphene grown by chemical vapor deposition (CVD) is transferred onto the wafer and etched into rectangular patterns. In addition to the sharpness of the graphene edge, the nanoscale gap between graphene and the palladium electrode (defined by the thickness of the $HfO_2$ layer) determines the strength of the electric field. Finally, photolithography is again performed to pattern Au electrodes, which formed Ohmic contacts to the graphene. The gate (Pd electrode) and contact electrodes are arranged in an interdigitated fashion to minimize series resistance and also create a large number of edges upon which to trap the particles and molecules. Bright-field optical microscope images of an example of a fabricated DEP device are shown in FIGS. 3C and 3D. The locations of the graphene films are outlined in FIG. 3C by the dashed rectangles.

DEP devices with electrodes formed from 2D materials have a variety of applications. The DEP device can be used for nanoscale manipulation and separation of particles. The DEP device can be used to trap various types of particles. The combination of nanoscale manipulation and trapping by the DEP device can be used to position a particle in a predefined location, e.g., location of a sensor. The trapping allows high-throughput and high sensitivity sensing of analytes with low molecule concentrations. This trapping scheme can seamlessly be integrated with sensors utilizing graphene transistors, varactors, nano-pores, nano-tips, or nanoribbons. The DEP device can be used for tunable mid-IR spectroscopy of ultralow-concentration molecules using graphene-based plasmonic resonators. The DEP device can be used to nano-position quantum emitters to build nanophotonic circuits or single-photon sources. The DEP system can be configured for DC readout with AC DEP trapping for electronic measurements of molecules.

One example of an application for a DEP device using graphene is in improving sensitivity of biochemical sensing. Performance of conventional graphene-based sensors are typically limited by the diffusive transport of target molecules to the surface, as the biomolecules still need to be placed at the region of highest sensitivity. For small-area nanostructures such as ribbons, nano-channels, or nano-pores, the challenge is compounded due to the small number of molecules that can be captured on the surface. The DEP device can precisely position nanoscale objects onto graphene-based nano-sensors for enhanced sensitivity.

Various types of particles that can be manipulated using the DEP device include DNA, molecules, biomolecules, cells, viruses, functionalized beads, biological particles, quantum dots, nano-beads, nano-diamonds, and nanoparticles.

For example, localization of nano-diamond particles on pre-fabricated devices in a rapid manner is highly desirable for applications in nano-sensing, but is very difficult to achieve due to their nanoscale size and aggressive Brownian motion in solutions. Trapping of 40 nm nano-diamond (ND) particles with nitrogen-vacancy (NV) centers ($\lambda_{em}$: 637 nm, Adamas Nanotechnologies) at the trapping sites on graphene (FIG. 7d) was demonstrated using the DEP device. The ND particles are carboxylate-modified to ensure facile dispersion in aqueous solution. Being a dielectric particle, the ND particles polarize in presence of a non-uniform electric field and are attracted towards the region of strongest electric field gradient due to positive DEP. Fluorescent images ($\lambda_{ex}$: 540-553 nm) collected after turning on the bias (amplitude 2 V and frequency 100 kHz) show ND particles localized at the trapping sites.

In general, the frequency of the applied AC bias can be varied to control DEP manipulation of different types of particles in various ways. Without wishing to be bound by theory, a sign of the DEP force can switch from positive to negative or vice versa around a crossover frequency. For example, a positive DEP force can be used to trap particles, and a negative DEP force can be used to repel or release particles. For example, for DNA molecules, frequency of 100 kHz can be used to loosely trap, or localize, the DNA molecules, 1 MHz can be used to tightly trap the DNA molecules, and frequency of 10 MHz can be used to release the DNA molecules. As another example, for polystyrene beads, 1 MHz can be used to tightly trap the polystyrene beads, and frequency of 10 MHz can be used to release the polystyrene beads.

Exact frequencies for trapping and releasing the particles can change based on various factors, including composition, size, geometry and polarizability of the particles, and characteristics of the fluid medium containing the particles, such as conductivity, dielectric permittivity and viscosity. As such, in general, the trapping frequency can be higher than the releasing frequency, and vice versa, based on the various factors associated with the particles and the fluid medium.

In general, certain types of particles (e.g., cells, molecules) can be selectively manipulated, trapped, or sorted using different AC bias frequencies based on the polarizability or chirality of different types of particles.

Examples

DEP Experiment Method

A solution volume of ~10 μl was placed on top of graphene electrodes, confined within a well made in adhesive tape. A cover slip was placed to avoid any unwanted evaporation. A probe station was used to apply an AC bias across the contact pads by a function generator (HP 33120A). The peak amplitude of the voltage used was in the range of 1 to 3 V. Depending on the particle, the frequency of the AC bias was optimized for polystyrene, DNA molecules, and nano-diamonds (ND). For the polystyrene and ND particles, water was used as a surrounding medium (conductivity ~4 S/cm), whereas 10 µM KCl solution (conductivity ~12 S/cm) was used for DNA.

DEP Manipulation of DNA

The DEP device including the first electrode 110 formed from graphene was used in demonstrating capturing of biomolecules. DNA molecules with 10 kbp and 500 bp tagged with YOYO-1 dye ($\lambda_{EF}$: 488 nm) at a final concentration of 10 pM in a 10 µM KCl solution was used for the demonstration. To predict the polarizability of the DNA molecules, a counterion fluctuation (CIF) model is often used, which depends on the redistributions of counterions around the charged sites present on the molecule. For this model to be valid, the concentration of counterions ($C_{ions}$) present in the solution should be much greater than the total number of charged sites present across all DNA molecules, as expressed by $$\frac{C_{ions}}{C_{DNA}} >> N_{ions/DNA} \quad (7)$$

where CDNA is the concentration of DNA and $N_{ions/DNA}$ represents the number of counterions required to saturate all the charged sites in a DNA molecule. Since there are 2 negative charges per base pair on a DNA molecule, the values of $N_{ions/DNA}$ for 10 kbp and 500 bp DNA are 20000 and 1000, respectively. As $C_{ions}$/CDNA (=$10^6$) is much higher than $N_{ions/DNA}$, the criterion in (4) is satisfied. The trapping force however must still be enough to overcome the thermal drag force (equation 2), which is contributed by the random diffusion of certain objects in a solution. The DEP force on a DNA molecule can be expressed by $$\vec{F}_{DEP} = \frac{1}{4}a\nabla|E|^2 \quad (8)$$

where α is the polarizability of the DNA molecule. The polarizability values were estimated from previously reported empirical findings that correspond to ~3.48×10⁻³¹ Fm² and ~1.00×10⁻³¹ Fm² for the 10 kbp and 500 bp DNA, respectively. Next, the threshold $\nabla|E|^2$ was calculated by equating the DEP force (equation 5) with the thermal force (equation 2). The diffusion coefficient (D) of 10 kbp DNA molecules is ~1.35 µm²/s, which can be used to calculate its hydrodynamic radius (Rh) using the equation $$R_h = \frac{k_B T_R}{6\pi\eta D} \quad (9)$$

where η=1.002×10⁻³ Pa-s is the viscosity of the surrounding medium (water). From equation 6, the hydrodynamic radius for a 10 kbp DNA molecule can be approximated as 162 nm that corresponds to an $F_T$ value of 12.7 fN (using equation 2). The threshold $\nabla|E|^2$ to trap a 10 kbp DNA molecules is ~1.46×10¹⁷ (using equation 5). For 500 bp DNA, the diffusion coefficient is ~6 µm²/s that corresponds to an Rh of ~36.45 nm and a $F_T$ of ~56.44 fN. The threshold $\nabla|E|^2$ for a 500 bp DNA molecule is ~2.26×10¹⁸.

Figure 7A:
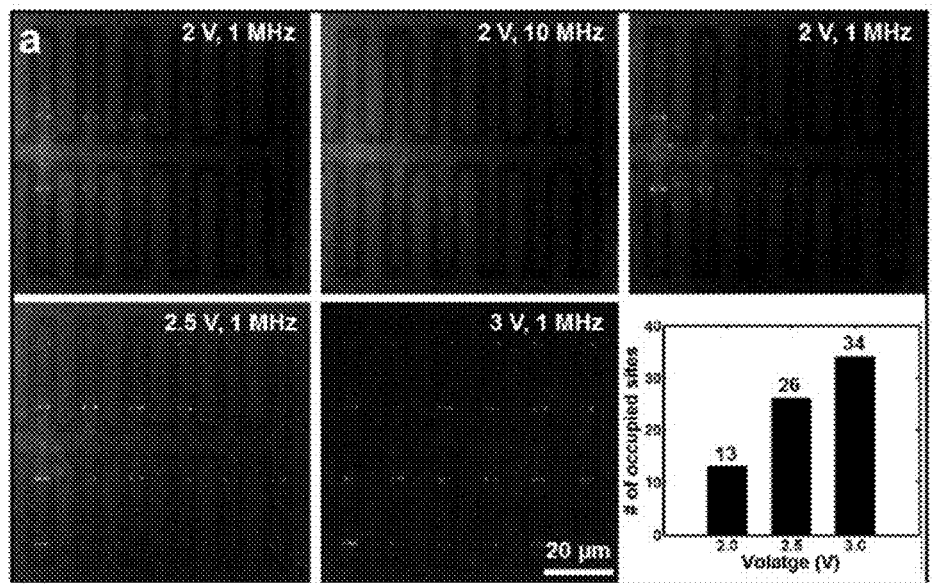
FIGS. 7A-7D shows DEP manipulation of 10 kbp DNA molecules and nano-diamonds.

FIG. 7a shows trapping and releasing of DNA molecules at an applied voltage of amplitude 2 V. A frequency of 1 MHz was used to capture the DNA molecules at the trapping sites. The efficiency of trapping goes down at higher frequencies, as the counterions present in the solution do not have enough time to redistribute in each cycle of the AC bias. Thus at 10 MHz the DNA molecules lose their polarizability and are released into the solution. The threshold $\nabla|E|^2$ to trap a 10 kbp DNA molecule is 1.46×10¹⁷, which can be readily achieved using graphene electrodes (FIG. 4b). However, a slightly higher voltage (2 V) was applied to achieve DEP manipulation, as the concentration of DNA used in this experiment was fairly low (10 pM). Applying a higher voltage increases the trapping volume, which is important to avoid diffusion limitations. This was further demonstrated by applying higher voltage amplitudes of 2.5 V and 3 V that improved the DNA capture efficiency as evident from the increased number of occupied trapping sites. The number of occupied trapping sites was measured as a function of the applied voltage (FIG. 7a). At 2 V, around 13 sites were occupied, which was increased to 26 at 2.5 V and 34 at 3 V.

Figure 7B:
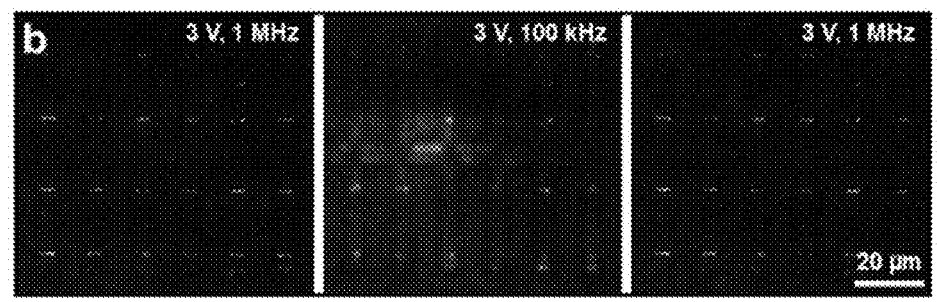

So far, DEP manipulation using high frequency AC fields (1 to 10 MHz) was shown. Reducing the frequency to 100 kHz, results in interesting localization of the DNA molecules near the graphene edge but the molecules are not tightly trapped at the edge (FIG. 7b). This phenomenon could be explained by generation of fluid flow at lower frequencies due to the formation of electrical double layers near the electrode surface. However, this mechanism depends on the charge relaxation frequency (f) of the system, which is given by $$f = \frac{\sigma_m}{2\pi\varepsilon_m} \quad (7)$$

For a solution of conductivity 12 µS/cm (10 µM KCl solution, measured by B-771 LAQUAtwin, Horiba Scientific), the charge relaxation frequency is 270 kHz (from equation 7). Hence, while operating at 100 kHz, the system has enough time to create electrical double layers, which can generate fluid flow due to electroosmosis. Increasing the solution conductivity will also increase the charge relaxation frequency. For instance, using a higher conductivity solution such as 1 mM KCl (conductivity 0.93 mS/cm), increases the relaxation frequency to 21 MHz. In this case, a similar DNA localization effect near the graphene edge even at 1 MHz was observed (supporting information). This effect can also be switched to the case of tight trapping along the edge of graphene, simply by switching to higher frequencies. FIG. 7b shows the switching between these two effects in a reversible fashion with tight trapping at 1 MHz and localization near graphene edge at 100 kHz.

Figure 7C:
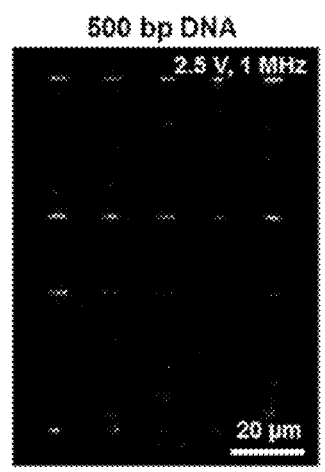
Figure 7D:
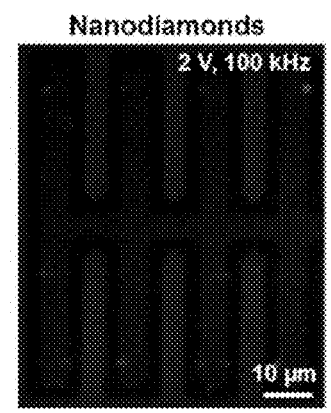

Next, 500 bp DNA molecules were used to demonstrate trapping of smaller DNA strands (FIG. 7c). The threshold $\nabla|E|^2$ to capture a 500 bp DNA molecule is 2.26×10¹⁸. From FIG. 4b, it is estimated that theoretically a 500 bp DNA molecule can be captured at a distance of 250 nm away from the graphene edge while applying an AC bias of amplitude 1.4 V. However, here a bias of amplitude 2.5 V was chosen to increase the range of trapping. Also, as 500 bp DNA molecules are extremely small in size, it was hard to observe single DNA molecule trapping at the trapping sites. Hence, the experiment was continued until trapping along the entire edge of graphene electrode was observed. The trapping experiment was completed within one minute.

DEP Manipulation of Polystyrene Nano-Beads

Applying an AC bias between the gate and the graphene electrode creates gradient forces along the graphene boundary (yellow lines in FIG. 5a), with the maximum $\nabla|E|^2$ at either end of the graphene electrode boundary (noted by red circles in FIG. 5a). These point junctions act as the region of strongest trapping potential because the $\nabla|E|^2$ is enhanced by both the graphene and the gate electrode edges. Therefore, a particle is expected to be selectively driven towards these junctions, called the "trapping sites." However, the entire boundary of the graphene electrode may also act as a DEP trap, albeit to a lesser extent than the trapping sites. The magnitude of the DEP force depends on the sharpness of the electrode boundaries as well as the 8 nm gap between the electrodes.

Polystyrene beads with 190 nm diameter were used to demonstrate efficient DEP trapping and releasing with sub-1 V bias voltages. The polarity of the DEP force depends on the frequency dependent CM factor ($f_{CM}(\omega)$) given by $$f_{CM}(\omega) = \frac{\varepsilon_p^*(\omega) - \varepsilon_m^*(\omega)}{\varepsilon_p^*(\omega) + 2\varepsilon_m^*(\omega)} \quad (6)$$

where $\varepsilon_p^*(\omega)$ and $\varepsilon_m^*(\omega)$ are the complex permittivities of the particle and the medium, respectively. Particles are attracted towards the trapping sites by positive DEP ($\text{Re}(f_{CM}(\omega)) > 0$) or are repelled from the trapping sites by negative DEP ($\text{Re}(f_{CM}(\omega)) < 0$). The frequency of the applied AC bias at which such transition takes place, $f_{CM}(\omega) = 0$, is called the crossover frequency. To predict the frequency response of the polystyrene beads in water (conductivity=4 µS/cm), the CM factor was plotted as a function of frequency (FIG. 5b). The crossover frequency is found to be 4 MHz. Hence, a frequency of 1 MHz was chosen for positive DEP and 10 MHz for negative DEP. Fluorescently labeled polystyrene beads ($\lambda_{EF}$: 470 nm, $\lambda_{EG}$: 525 nm) were used to visualize the DEP manipulation capability of graphene electrodes using a 50×objective. A green background was observed before applying a voltage (FIG. 5c), which comes from the bulk solution. As soon as a bias of amplitude 750 mV was turned on, beads were selectively trapped at the trapping sites, which provide the maximum DEP force as discussed above (FIG. 5d). Of the 40 available trapping sites (4 sites on each finger electrode), ~34 of them was seen to be occupied. The trapped particles could be released due to negative DEP, simply by switching the frequency to 10 MHz (FIG. 5e). Particles were trapped again by switching to the positive DEP mode—showing the reversible nature of DEP manipulation (FIG. 5f). After switching to the positive DEP mode for the second time, all 40 trapping sites were occupied. It should also be noted that in some finger electrodes more beads could be observed along the graphene edge (the yellow line in FIG. 5a), which could be due to 1) the entire boundary of the graphene electrode could potentially present a fringe electric field that is responsible for DEP and 2) random sharp protrusions along the edge that can enhance the electric field gradient and possibly act as a DEP trap.

Low-Power DEP Trapping with Graphene Electrodes

Figure 6A:
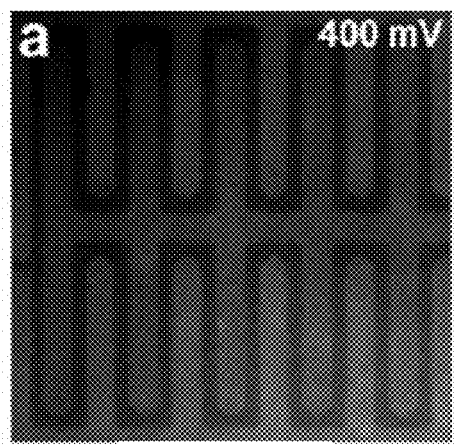
FIGS. 6A-6E shows voltage dependence of polystyrene bead trapping.
Figure 6B:
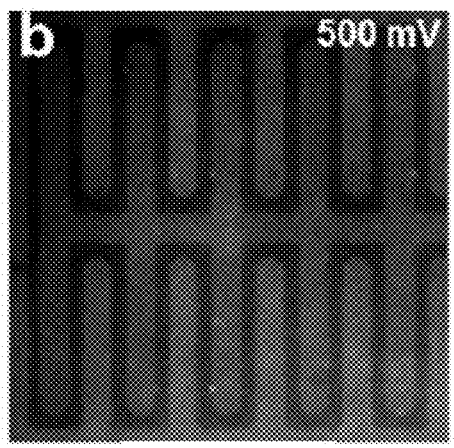
Figure 6C:
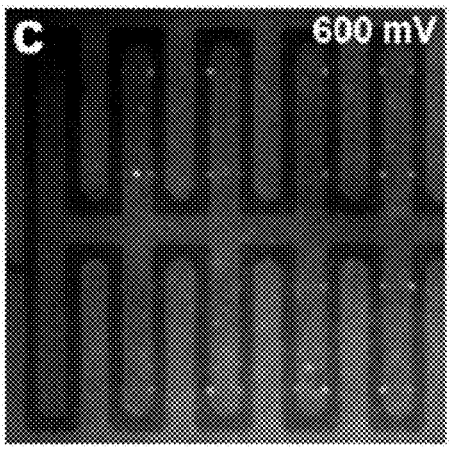
Figure 6D:
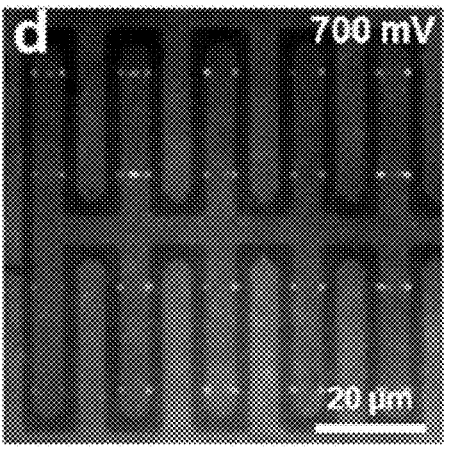
Figure 6E:
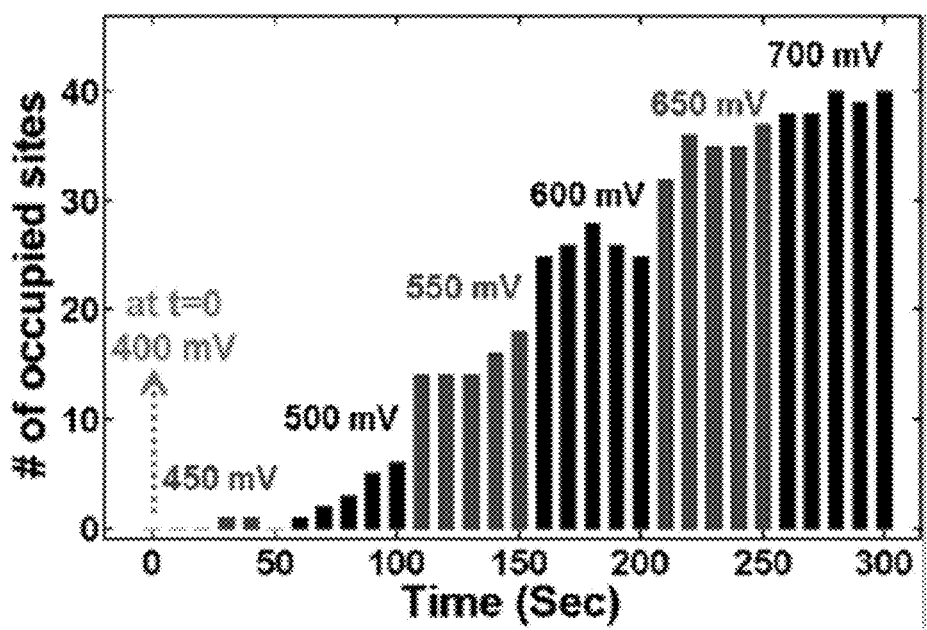

A voltage dependence study was performed to determine the minimum trapping voltage ($V_{min}$) for 190 nm polystyrene beads. This is the voltage at which the DEP force is enough to overcome the Brownian motion of the nanoparticles due to their thermal energy. The amplitude of the applied voltage was increased from 400 mV to 700 mV at a step interval of 50 mV. At each voltage, fluorescence images were collected for 50 s. More beads were trapped at the trapping sites as the voltage amplitude was increased (FIGS. 6a-d). To quantify this further, the number of occupied trapping sites as a function of the applied voltage was calculated (FIG. 6e). The first data point represents 400 mV, where no trapping was observed (FIG. 6a). At 500 mV, clear trapping of polystyrene beads could be observed at multiple trapping sites (circled in FIG. 6b). Trapping at more sites was observed at higher voltages (FIG. 6c) and at 700 mV all 40 sites were occupied (FIG. 6d). From this study, the $V_{min}$ for 190 nm beads was found to be 500 mV, where at least one trapping site was fully occupied for the entire duration.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A device comprising:
   a cell defining at least one channel extending in a first direction;
   a first electrode and a second electrode electrically isolated from the first electrode, at least one of the first and second electrodes being formed from a two-dimensional (2D) material extending in a plane parallel to the first direction; and
   a dielectric layer between the first electrode and the second electrode,
   wherein the first and second electrodes are arranged relative to the channel such that application of a sufficient voltage across the first and second electrodes generates an electric field having an electric field gradient sufficient to apply a dielectrophoretic force on a particle in the channel.

2. The device of claim 1, wherein the dielectric layer comprises a dielectric material selected from the group consisting of silicon oxide, hafnium oxide, zirconium oxide, titanium oxide, zinc oxide, boron nitride, aluminum oxide, and silicon nitride.

3. The device of claim 1, further comprising a gap between the first electrode and the second electrode, wherein the gap is in fluid communication with the at least one channel.

4. The device of claim 1, wherein the two dimensional (2D) material is a non-metal material.

5. The device of claim 1, wherein the two dimensional (2D) material is selected from the group consisting of graphene, molybdenum disulphide, molybdenum diselenide, molybdenum diteluride, tungsten disulphide, tungsten diselenide, and phosphorene.

6. The device of claim 1, wherein the two dimensional (2D) material is a single-layer two dimensional (2D) material.

7. The device of claim 1, wherein the two dimensional (2D) material is a few-layer two dimensional (2D) material.

8. The device of claim 1, wherein the first and second electrodes are spaced apart by a distance of 1 nm to 50 nm.

9. The device of claim 8, wherein the channel is formed by the separation between the first and second electrodes.

10. The device of claim 1, wherein the first and second electrodes are configured such that application of a voltage of 5V or less across the first and second electrodes generates an electric field gradient in at least part of the channel sufficient to apply the dielectrophoretic force on the particle in the channel.

11. A varactor comprising the device of claim 1, first and second electrodes being electrodes of the varactor.

12. A field effect transistor comprising the device of claim 1, first and second electrodes being electrodes of the field effect transistor.

13. A system for applying a dielectrophoretic force on a particle, the system comprising:
the device of claim 1;
a voltage source for applying the sufficient voltage across the first and second electrodes.

14. The system of claim 13, wherein the voltage source is an on-chip voltage source.

15. The system of claim 13, further comprising an optical imaging device for observing the particle while the voltage source applies the voltage.

16. The system of claim 15, wherein the optical imaging device is a microscope.

17. The system of claim 13, wherein the device comprises a varactor comprising the first and second electrodes.

18. The system of claim 17, further comprising an electrical detection device for electrically detecting the particle while the voltage source applies the voltage.

19. A device comprising:
a cell defining at least one channel;
a first electrode and a second electrode electrically isolated from the first electrode, at least one of the first and second electrodes being formed from a two-dimensional (2D) material, wherein the first electrode and the second electrode are non-parallel finger electrodes
a dielectric layer between the first electrode and the second electrode,
wherein the first and second electrodes are arranged relative to the channel such that application of a sufficient voltage across the first and second electrodes generates an electric field having an electric field gradient sufficient to apply a dielectrophoretic force on a particle in the channel.

20. A method comprising:
confining a particle to a channel extending in a first direction, the channel being adjacent a first electrode and a second electrode electrically isolated from the first electrode, at least one of the first and second electrodes being formed from a two dimensional (2D) material extending in a plane parallel to the first direction, a dielectric layer being arranged between the first electrode and the second electrode; and
applying a voltage to the first and second electrodes, to generate an electric field gradient sufficient to apply a dielectrophoretic force on the particle in the channel.

* * * * *